(12) United States Patent
Guthrie et al.

(10) Patent No.: US 6,312,687 B1
(45) Date of Patent: Nov. 6, 2001

(54) STABILIZED LACTOPEROXIDASE AND GLUCOSE OXIDASE CONCENTRATE

(75) Inventors: Walter Graham Guthrie; David Vincent Roper, both of Nottingham (GB)

(73) Assignee: Knoll Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/403,652
(22) PCT Filed: Apr. 24, 1998
(86) PCT No.: PCT/EP98/02451
 § 371 Date: Oct. 25, 1999
 § 102(e) Date: Oct. 25, 1999
(87) PCT Pub. No.: WO98/49272
 PCT Pub. Date: Nov. 5, 1998

(30) Foreign Application Priority Data

Apr. 29, 1997 (GB) .................................................. 9708641

(51) Int. Cl.⁷ ............................ A61K 38/54; A61K 38/43
(52) U.S. Cl. ...................... 424/94.3; 424/94.1; 424/94.2
(58) Field of Search .................................. 424/94.1, 94.2, 424/94.3, 94.4

(56) References Cited

U.S. PATENT DOCUMENTS 5,453,284   9/1995   Pellico ................................. 424/94

FOREIGN PATENT DOCUMENTS

| 88/02600 | 4/1988 | (WO) . |
| 90/05182 | 5/1990 | (WO) . |
| 91/11105 | 8/1991 | (WO) . |
| 92/01466 | 2/1992 | (WO) . |
| 95/10605 | 4/1995 | (WO) . |
| 95/26137 | 10/1995 | (WO) . |

*Primary Examiner*—Jon P. Weber
*Assistant Examiner*—Patricia Patten
(74) *Attorney, Agent, or Firm*—Keil & Weinkauf

(57) ABSTRACT

A stabilized aqueous enzyme concentrate composition which comprises:
 a) 1000 to 1800 units/ml of lactoperoxidase;
 b) 1500 to 2750 units/ml of glucose oxidase;
 c) 10 to 20% w/v of an alkali metal halide salt; and
 d) a chelating buffering agent present in an amount such that the pH of the composition is in the range of 5.5 to 6.5.

8 Claims, 1 Drawing Sheet

STABILIZED LACTOPEROXIDASE AND GLUCOSE OXIDASE CONCENTRATE

Figure 1:
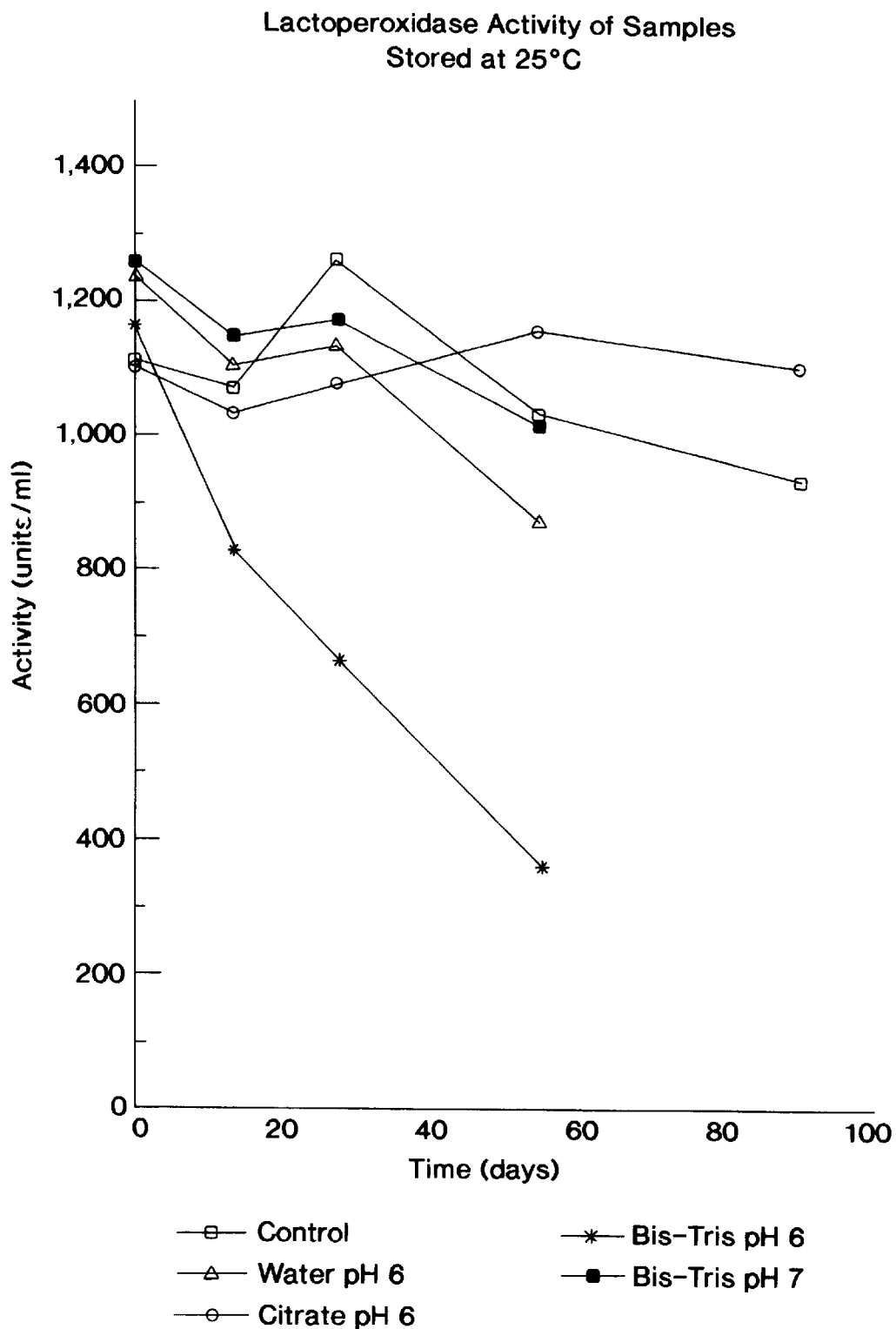

This is a 371 of PCT Application No. PCT/EP 98/02541, filed on Apr. 24, 1998.

This invention relates to a stabilized enzyme concentrate of glucose oxidase and lactoperoxidase.

WO91/11105 discloses anti-microbial compositions which contain iodide and hiocyanate anions, glucose oxidase, D-glucose and lactoperoxidase. These compositions have excellent anti-microbial properties and are effective against bacteria, yeasts and moulds. It is further disclosed that the compositions may be provided in concentrated substantially non-reacting form. Such concentrated compositions maintain physical separation of the glucose oxidase and at least one of its substrates, namely D-glucose, water and oxygen, such that $H_2O_2$ production is substantially prevented during storage. It is also disclosed that the concentrated compositions may incorporate at least one buffering agent to minimize the fall of the pH which may otherwise occur after activation of the concentrated composition. However, although a very successful product exists in which D-glucose, sodium thiocyanate and potassium iodide are provided in a substrate solution and the lactoperoxidase and glucose oxidase are provided in a concentrated enzyme solution, there exists a problem with the enzyme solution regarding its comparatively short shelf-life which is around twelve weeks at ambient temperature. Therefore, there is a need to provide an enzyme solution with a much longer shelf-life.

It is known that the stabilization of an enzyme in solution is difficult. WO90/05182 describes some of the attempts which have been made to overcome this problem, for example the addition of sugars or glycerol to enzyme solutions or by freeze drying. WO90/05182 states that freeze drying is expensive and often results in denaturation and then discloses a method of protecting proteins against denaturation on vacuum or air drying which comprises mixing an aqueous solution of the protein with a soluble cationic polyelectrolyte and a cyclic polyol, and removing the water from the solution.

A method of stabilizing proteins in solution is disclosed in WO95/10605 in which a protein stabilizer additive which comprises two or more of a tris compound of formula I: $(HOCH_2)_3$—C—R, wherein R is various groups for example $C_{1-4}$ alkyl which may be optionally substituted, a polvelectrolyte; a buffer and one or more further components for example, divalent metal salts. On page 3 of this document it is disclosed that "The said further component may be selected from the group comprising divalent metal ions, chelators, for example EDTA, EGTA or citrate (not with peroxidases) or polyols". The statement would direct the person skilled in the art, faced with the problem of formulating a stable enzyme concentrate containing lactoperoxidase, away from the use of citrates. It would point him instead to the use of non-chelating buffers, for example BIS/TRIS.

It will be appreciated that, given the known difficulties of stabilizing one enzyme in solution, the problem is further compounded when a stable mixture of two enzymes in solution is required since each enzyme has its own optimum requirements which may not be compatible with the optimum requirements of the other enzyme. In addition, it is not only required that the enzyme concentrate is chemically stable but it must also be preserved against microbial attack if it is to be used in anti-microbial compositions. There may be incompatibility between the agent(s) required to produce chemical stability and the agent required to produce preservation.

The present invention provides a stabilized aqueous enzyme concentrate composition which comprises:
a) 1000 to 1800 units/ml of lactoperoxidase;
b) 1500 to 2750 units/ml of glucose oxidase;
c) 10 to 20% w/v of an alkali metal halide salt; and
d) a chelating buffering agent present in an amount such that the pH of the composition is in the range of 5.5 to 6.5.

Although it is known that sodium chloride may be used to preserve lactoperoxidase, for example at a level of 1.8% or 12%, it is nevertheless surprising that a concentrate of lactoperoxidase and glucose oxidase may be stabilized chemically and microbially preserved for long periods by a combination of a chelating buffering agent and an alkali metal salt.

WO95/26137 (page 43) discloses the effect of pH on the anti-microbial activity of final compositions which have been prepared by combining and diluting two concentrates (Phase A and Phase B) to 0.9% and 0.05%.

| Component | Concentration |
|---|---|
| Phase A | |
| | (w/v %) |
| D-glucose | 45 to 55 |
| Sodium thiocyanate | 0.42 to 0.52 |
| Potassium iodide | 0.66 to 0.80 |
| Phase B | |
| Lactoperoxidase | 5,500 Units/ml |
| Glucose oxidase | 2,250 Units/ml |

The pH of each phase was adjusted to between 5.5 and 6.5 with buffer solutions. The pH of each combined concentrate mixture after dilution was adjusted using a citrate/phosphate buffer. However, this document does not disclose or suggest the unexpected and beneficial effect of obtaining an enzyme concentrate which is stable over a prolonged period.

EP 307,376 and WO91/11105 disclose diluted anti-microbial compositions which contain citrate salts and/or sodium chloride. However, there is no disclosure of a stabilised enzyme concentrate according to the present invention.

EP 252,051 discloses a method of stabilizing lactoperoxidase in milk products, foodstuffs and pharmaceuticals to which the enzyme lactoperoxidase has been added, wherein the product containing lactoperoxidase is adjusted with regard to pH, so that the pH is in the range 3.25 to 6 at the dissolution in water. It does not disdose a stabilised enzyme concentrate according to the present invention.

Suitably, the enzyme concentrate is stable for at least 6 months. Preferably the enzyme concentrate is stable for at least 9 months. More preferably the enzyme concentrate is stable for at least 12 months. Most preferably the enzyme concentrate is stable for at least 18 months.

The stability of the enzyme concentrate is determined by assaying the activity of the lactoperoxidase and glucose oxidase at regular intervals using standard assay techniques which are given in the examples of this specification. The efficacy of antimicrobial preservation is assessed using the British Pharmacopeia test as given in the 1993 volume, Appendix XVIC A191.

Suitably the stability of the enzyme concentrate is such that the activities of lactoperoxidase and glucose oxidase are maintained at at least 60% of their original activity over the time period examined. Preferably the activities of lactoperoxidase and glucose oxidase are maintained at least 75% of their original activity after storage for 6 months at 25° C. More preferably the activities of lactoperoxidase and glucose oxidase are maintained at least 75% of their original activity after storage for 12 months at 25° C.

Preferably the alkali metal halide is selected from sodium chloride, potassium chloride, sodium bromide, potassium bromide, sodium iodide or potassium iodide or mixtures thereof. More preferably the alkali metal halide is sodium chloride.

Preferably the concentration of the alkali metal halide is in the range of 12 to 18% w/v. More preferably the concentration of the alkali metal halide is in the range of 14 to 16% w/v. Most preferably the concentration of the alkali metal halide is in the range of 14.5 to 15.5% w/v.

Suitably the chelating buffering agent is selected from one or more of the following: alkali metal salts of citric, phthalic, tartaric, adipic or succinic acid. Preferably the chelating buffering agent is trisodium citrate. Suitably the amount of chelating buffering agent present is that required to give a final pH of in the range 5.5 to 6.5. Preferably the amount of buffering agent is such that the pH of the composition is in the range 5.7 to 6.2. Most preferably the amount of buffering agent present is such that the pH of the composition is in the range of 5.9 to 6.1. Optionally monosodium orthophosphate may be present in an amount ranging from 0.05 M to 0.5 M, preferably 0.25 M. Preferably the weight of trisodium citrate used is in the range 0.5 to 1.5% w/v.

The invention will be understood with reference to the following non-limiting tests and examples.

Effect of Buffer

Five different solutions of lactoperoxidase and Glucox PS were examined in this study:
a) Standard Enzyme Concentrate Solution
b) Lactoperoxidase and Glucox PS in water at pH 6.0
c) Lactoperoxidase and Glucox PS in 50 mM citrate buffer pH 6.0
d) Lactoperoxidase and Glucox PS in 50 mM BIS-TRIS buffer pH 6.0
e) Lactoperoxidase and Glucox PS in 50 mM BIS-TRIS buffer pH 7.0

| Glucose PS is a freeze dried preparation of Glucose Oxidase | | |
|---|---|---|
| Solution a) | Lactoperoxidase | 1000–1800 U/ml |
| | Glucose oxidase | 1500–2750 U/ml |
| | pH | 5.5 to 6.5 |
| | Wt/ml at 20° C. | 1.00 to 1.02 g. |

Solutions b) to e) were made up as follows.
A mixture of 1.6 1 of lactoperoxidase (2800 units/ml) and Glucox PS (4250 units/ml) in water for injection (WFI) was made up.

$$\text{The weight of lactoperoxidase required (g)} = \frac{2800 \times 1600}{\text{Activity (units/mg)} \times 1000}$$

$$\text{The weight of Glucox PS required (g)} = \frac{4250 \times 1600}{\text{Activity (units/mg)} \times 1000}$$

The above solution was divided into 4 equal parts (i to iv) and the following materials were added.
i) nothing
ii) 8.405 g citric acid
iii) 8.368 g BIS/TRIS
iv) 8.368 g BIS/TRIS The volume of the solutions i to iv were made up to 750 ml with WFI.

The pH of each of the above solutions was adjusted using 1 M NaOH or 1 M HCl as appropriate, to:
i) 5.9 to 6.1
ii) 5.9 to 6.1
iii) 5.9 to 6.1
iv) 6.9 to 7.1

The volume of the solutions i to iv were made up to 800 ml with WFI.

All five solutions were divided into 25×30 ml samples. One sample of each was retained for analysis as the initial sample and eight samples of each were stored at 4° C., 25° C. and 40° C.

The solutions were assayed as described in the table below by the assay methods for glucose oxidase and lactoperoxidase which are described later.

| Temp (° C.) | Initial | 3 days | 1 week | 2 weeks | 1 month | 2 months | 4 months |
|---|---|---|---|---|---|---|---|
| 4 | — | | | L | L | L | L |
| 25 | L, G, pH | | | | L, G, pH | L, pH | L, G, pH |
| 40 | — | L | L | L | L | L | |

L = lactoperoxidase activity
G = glucose oxidase activity
B = pH (after other assays have been successfully completed)

The results are shown in Tables 1, 2 and 3 and FIG. 1.

TABLE 1

| Glucose Oxidase Activities (units/ml) | | | | | |
|---|---|---|---|---|---|
| | | | | 91 Days | |
| | Initial | 28 Days | 4° C. | 25° C. | 40° C. |
| Control | 1778 | 2166 | 1922 | 1561 | 103 |
| WFI | 1867 | 2110 | | nd | |
| Citrate | 1532 | 1956 | 1611 | 1617 | 5.5 |
| Bis-Tris pH 6.0 | 1814 | 1568 | | nd | |
| Bis-Tris pH 7.0 | 1957 | 1754 | | nd | | nd = not done

TABLE 2

| Lactoperoxidase Activities (units/ml) | | | | | | | |
|---|---|---|---|---|---|---|---|
| Sample | | Initial | 3 Days | 7 Days | 14 Days | 28 Days | 55 Days | 91 Days |
| Con-trol | 4° C. | | | | 1258 | 1325 | 1559 | 1713 |
| | 25° C. | 1305 | | | 1070 | 1265 | 1031 | 935 |
| | 40° C. | | | 1051 | 734 | 737 | 516 | 502 | 733 |
| WFI | 4° C. | | | | 1173 | 1323 | 1289 | |
| | 25° C. | 1237 | | | 1103 | 1134 | 872 | |
| | 40° C. | | | 951 | 1028 | 956 | 328 | 572 | |
| Ci-trate | 4° C. | | | | 974 | 1130 | 1199 | 1417 |
| | 25° C. | 1100 | | | 1031 | 1077 | 1156 | 1104 |
| | 40° C. | | | 1040 | 997 | 1137 | 930 | 973 | 1092 |
| Bis-Tris pH 6.0 | 4° C. | | | | 1153 | 1274 | 1374 | |
| | 25° C. | 1163 | | | 839 | 665 | 359 | |
| | 40° C. | | | 869 | 446 | 233 | 168 | 30.2 | |
| Bis-Tris | 4° C. | | | | 1192 | 1301 | 1378 | |
| | 25° C. | 1257 | | | 1147 | 1174 | 1017 | |

TABLE 2-continued

| | Lactoperoxidase Activities (units/ml) | | | | | |
|---|---|---|---|---|---|---|
| Sample | Initial | 3 Days | 7 Days | 14 Days | 28 Days | 55 Days | 91 Days |
| pH 7.0 40° C. | | 1071 | 962 | 845 | 637 | 545 | |

TABLE 3 pH of Samples of Lactoperoxidase and Glucose Oxidase Stored at Various Temperatures

| Sample | Initial | 14 Days | 28 Days | 55 Days | 91 Days |
|---|---|---|---|---|---|
| Control | | | | | |
| 4° C. | nd | 6.08 | 6.08 | 6.10 | 6.10 |
| 25° C. | nd | 6.04 | 6.07 | 6.06 | 6.07 |
| 40° C. | nd | 6.06 | 6.04 | 6.02 | 5.99 |
| WFI | | | | | |
| 4° C. | nd | 5.89 | 6.03 | 6.14 | nd |
| 25° C. | 6.00 | 6.13 | 6.23 | 6.40 | nd |
| 40° C. | nd | 6.10 | 6.32 | 6.39 | nd |
| Citrate | | | | | |
| 4° C. | nd | 6.04 | 6.01 | 6.03 | 6.05 |
| 25° C. | 6.00 | 6.01 | 6.05 | 6.16 | 6.42 |
| 40° C. | nd | 6.07 | 6.08 | 6.11 | 6.17 |
| Bis-Tris pH 6.0 | | | | | |
| 4° C. | nd | 5.84 | 5.98 | 5.94 | nd |
| 25° C. | 6.00 | 5.59 | 5.64 | 5.36 | nd |
| 40° C. | nd | 5.26 | 5.30 | 5.00 | nd |
| Bis-Tris pH 7.0 | | | | | |
| 4° C. | nd | 6.97 | 7.03 | 7.02 | nd |
| 25° C. | 7.00 | 6.87 | 6.93 | 6.91 | nd |
| 40° C. | nd | 6.83 | 6.90 | 6.81 | nd |

Effect of Buffer and Alkali Metal Salt

A citrate buffer was prepared by dissolving citric acid monohydrate (52.53 g) in approximately 3.5 l water for injection (WFI). The buffer solution was split into 5 equal aliquots of 700 ml. Sodium chloride (150 g) was added to the first aliquot and the pH of this test solution was adjusted to between 5.9 and 6.1 with 6 M NaOH. Sufficient lactoperoxidase and glucose oxidase were added to give a test solution containing 1500 U/ml lactoperoxidase and 2125 U/ml glucose oxidase.

$$\text{Weight of lactoperoxidase (g)} = \frac{1500 \times 1000}{\text{activity} \times 1000}$$

$$\text{Weight of glucose oxidase (g)} = \frac{2125 \times 1000}{\text{activity} \times 1000}$$

The pH of the test solution was adjusted to between 5.9 and 6.1 with 6 M NaOH. The volume of the test solution was made up to 1.0 l with WFI.

100 ml of the test solution was submitted for BP challenge testing and the remainder of the test solution was split into 19 samples of 40 ml.

The samples were stored and assayed as indicated in the table below.

| Temp (° C.) | Time (months) | | | | | | | | | |
|---|---|---|---|---|---|---|---|---|---|---|
| | 0 | 0.5 | 1 | 2 | 3 | 4 | 5 | 6 | 9 | 12 |
| 4 | | | L | | L | | | L | | L |
| 25 | L, G, B | L | L | L | L, G | L | L | L, G | L, G | L, G |
| 40 | | L | L | L | L, G | | | L, G | | |

L = lactoperoxidase assay
G = glucose oxidase assay
B = BP challenge

The results are given in Tables A, B, C, D and E. The results confirm that the activity of both enzymes was maintained.

ENZYMATIC ASSAY OF LACTOPEROXIDASE

All reagents and sample solutions were prepared fresh daily. Purified water. HPLC grade as supplied by Romil Chemicals was suitable.

Phosphate Buffer (0.1 M pH 5.5)

(a) Potassium dihydrogen phosphate (1.361 g) was weighed into a 100 ml graduated flask, dissolved in and diluted to volume with purified water.

(b) Dipotassium hydrogen phosphate trihydrate (2.282 g) was weighed into a 100 ml graduated flask, dissolved in and diluted to volume with purified water.

To 50 ml of solution (a) was added sufficient solution (b) to give pH 5.5.

ABTS Solution

ABTS solution (100 mM) was prepared by dissolving 2,2'-Azino-bis-(3-ethylbenzthiazoline-6-sulphonic acid) diammonium salt (ABTS) (0.55 g) in 10 ml of purified water.

Hydrogen Peroxide Solution 0.1 ml of 30% hydrogen peroxide solution was dissolved in 120 ml of purified water. The absorbance of this solution was measured at 240 nm in 1-cm cells and adjusted if necessary by further additions of hydrogen peroxide or purified water to give an absorbance reading of about 0.40.

Dipotassium Hydrogen Phosphate Solution (0.2 M)

Dipotassium hydrogen phosphate trihydrate (22.820 g) was dissolved in 500 ml of purified water.

Strong Sample Solution 1.0 ml of the sample was pipetted into a 200 ml graduated flask and diluted to volume with 0.2 M dipotassium hydrogen phosphate solution.

Dilute Sample Solution 1.0 ml of the strong sample solution was pipetted into a 200 ml graduated flask and diluted to volume with 0.2 M dipotassium hydrogen phosphate solution.

Procedure 2.20 ml of phosphate buffer, 0.70 ml of ABTS solution and 0.10 ml of hydrogen peroxide solution were pipetted into a 1 cm silica or glass cuvette and mixed. The sample was equilibrated in a water bath at 25° C. then 0.020 ml of dilute sample solution was added. The sample was mixed and again equilibrated at 25° C. for 30 seconds. The cell was immediately transferred to the spectrophotometer and the change in absorbance was measured over a period of 2 minutes at a wavelength of 436 nm. The change in absorbance per minute was calculated. The above procedure was carried out in triplicate and the mean change in absorbance per minute (−A/min) for the three determinations was calculated.

$$\text{Then: lactoperoxidase (units/ml)} = \frac{3.02}{29.3} \times \frac{200}{1} \times \frac{5}{1} \times \frac{-A/\min}{0.02}$$

ENZYMATIC ASSAY OF GLUCOSE OXIDASE

All reagents and sample solutions were prepared fresh daily. Purified water. HPLC grade as supplied by Romil Chemicals was suitable.

Citric Buffer pH5

Citric acid monohydrate (10.08 g) was weighed into a 500 ml graduated flask, 100 ml of M sodium hydroxide solution was added and the solution diluted to volume with purified water.

Benzoquinone Solution

Benzoquinone (puriss) (0.05 g) was weighted into a 50 ml graduated flask, dissolved in and diluted to volume with purified water.

Glucose Solution

Anhydrous D-glucose (18.0 g) was weighed into a 100 ml graduated flask, dissolved in and diluted to volume with purified water. The solution was allowed to stand for 24 hours before use.

Strong Sample Solution 5.0 ml of the sample solution was pipetted into a 100 ml graduated flask and diluted to volume with citrate buffer.

Dilute Sample Solution 5.0 ml of strong sample solution was pipetted into a 100 ml graduated flask and diluted to volume with citrate buffer. Benzoquinone solution (2.0 ml) and 1.0 ml of glucose solution were pipetted into each of two 1 cm silica cuvettes. Into one cell 1.0 ml of citrate buffer was pipetted. The solution was mixed by inversion and placed in the reference cell compartment of the spectrophotometer. Into the other cell was pipetted 0.95 ml of citrate buffer. The solution was mixed and allowed to equilibrate at 25° C. in a water bath. The cell was placed in the sample compartment of the spectrophotometer and the instrument was zeroed. 0.05 ml of dilute sample solution was added to the sample cell. The sample was mixed by inversion and the change in absorbance was immediately recorded over a period of 1–2 minutes at a wavelength of 290 nm. The change in absorbance per minute was calculated. The above procedure was carried out in triplicate and the mean change in absorbance per minute (−A/min) for the three determinations was calculated.

$$\text{Then: glucose oxidase (units/ml)} = \frac{-A/\min}{2.31} \times \frac{4.0}{0.05} \times \frac{100}{5} \times \frac{100}{5}$$

BP Test

The test for the efficacy of Antimicrobial Preservation was carried out using a modification of the method described in the British Pharmacopeia 1993 Appendix XVIC A191 using the following test organisms:

*Aspergillus niger* IMI 149 007

*Candida albicans* (ATCC 10231)

*Pseudomonas aeriginosa* (NCIMB 8626)

*Staphylococcus aureus* (NCIMB 9518).

*Saccharomyces cerevisiae* (NYC 87)

mixed bacterial inoculum based on:

*S. aureus, S. epidermidis* and *Streptococcus haemolyticus*.

These were used at two challenge levels, namely $10^6$ per ml and $10^2$ per ml in separate tests.

The criteria of acceptance used, were as given in the 1995 addendum to the British Pharmacopeia in Appendix XVII F A407 and are shown below:

|  |  | Log reduction | | | |
|---|---|---|---|---|---|
|  |  | 2d | 7d | 14d | 28d |
| Bacteria | A | 2 | 3 | — | NI |
|  | B | — | — | 3 | NI |
| Fungi | A | — | — | 2 | NI |
|  | B | — | — | 1 | NI |

The A criteria express the recommended efficacy to be achieved. In justified cases where the A criteria cannot be attained, for example, for reasons of an increased risk of adverse reactions, the B criteria must be satisfied.

NI: No increase; d = days.

Due to intended use of the stabilised enzyme solution and the low risk of contamination and spoilage after manufacture, it was deemed appropriate to modify the above criteria. The pass requirements were based on the B criteria with the exception that absence of growth for the Gram positive bacteria after inoculation was judged to be acceptable.

The stabilised described previously was tested both initially and after 6 months storage and was found to be acceptably preserved when submitted to the above modified test.

TABLE A

| Lactoperoxidase Activity U/ml versus time stored at 4° C. | | | | | |
|---|---|---|---|---|---|
| Activity | TIME (months) | | | | |
| (U/ml) | 0 | 1 | 3 | 6 | 12 |
| Dil 1 | 1463.6 | 1379.8 | 1619.4 | 1691.1 | 1163 |
|  | 1566.1 | 1327.2 | 1726.3 | 1324.5 | 1432 |
|  | 1515.8 | 1380.6 | 1668.6 | 1495.5 | 655 |
| Mean | 1515.0 | 1362.5 |  |  | 1083 |
| Dil 2 | 1403.0 | 1244.9 | 1776.4 | 1140.4 | 918 |
|  | 1743.9 | 1508.5 | 1952.3 | 1733.9 | 1022 |
|  | 1480.9 |  | 1915.2 | 1587.4 | 1207 |
|  | 1444.9 |  |  |  |  |
| Mean | 1518.2 | 1376.7 |  |  | 1049 |
| Combined Mean | 1516.6 | 1369.6 | 1776.2 | 1495.4 | 1066 |

TABLE B

Lactoperoxidase Activity U/ml versus time stored at 25° C.

| Activity (U/ml) | \ | \ | \ | TIME (months) | \ | \ | \ | \ |
|---|---|---|---|---|---|---|---|---|
|  | 0 | 0.5 | 1 | 2 | 3 | 4 | 5 | 6 | 12 |
| Dil 1 | 1463.6 | 1547.6 | 954.6 | 1541.7 | 2832.6 | 1738.1 | 2033.4 | 892.0 | 986 |
|  | 1566.1 | 1509.2 | 843.2 | 1429.6 | 2382.0 | 1354.3 | 1787.2 | 1241.7 | 1110 |
|  | 1515.8 | 1583.5 | 971.6 | 1417.1 | 2079.7 | 2100.6 | 1795.4 | 1816.9 | 1057 |
|  |  |  |  | 1536.3 |  |  |  |  | 1051 |
| Mean | 1515.0 | 1546.8 | 923.2 |  |  | 1731.0 | 1872.0 |  | 1950 |
| Dil 2 | 1403.0 | 1351.5 | 1070.6 | 1813.1 | 2067.8 | 2244.8 | 1766.5 | 1772.6 | 1983 |
|  | 1743.9 | 1517.1 | 1037.2 | 1734.7 | 2209.4 | 2137.5 | 2058.3 | 1883.9 | 1687 |
|  | 1480.9 |  | 955.5 | 1926.3 | 1915.9 | 2126.6 | 2050.2 | 1702.1 |  |
|  | 1444.9 | 1621.4 |  |  |  |  |  |  | 1873 |
| Mean | 1518.2 | 1496.6 | 1021.2 |  |  | 2169.6 | 1958.3 |  | 1462 |
| Combined Mean | 1516.6 | 1521.7 | 972.2 | 1628.4 | 2247.9 | 1870.2 | 1915.1 | 1551.5 | 1706 |

TABLE C

Lactoperoxidase Activity U/ml versus time stored at 4° C.

| Activity (U/ml) | 0 | 0.5 | 1 | 2 | 3 | 6 |
|---|---|---|---|---|---|---|
| Dil 1 | 1463.6 | 2423.2 | 1255.1 | 1386.5 | 1885.9 | 2125.2 |
|  | 1566.1 | 2455.4 | 1045.0 | 1398.8 | 1635.3 | 2049.8 |
|  | 1515.8 | 1941.2 | 1168.0 | 1502.7 | 1645.9 | 2232.6 |
| Mean | 1515.0 | 2273.2 | 1156.0 |  |  |  |
| Dil 2 | 1403.0 | 2452.9 | 1103.6 | 1434.4 | 2333.8 | 1990.9 |
|  | 1743.9 | 1970.6 | 975.2 | 1702.3 | 1027.4 | 1937.9 |
|  | 1480.9 | 2107.1 | 1002.7 |  | 1529.3 | 1789.6 |
|  | 1444.9 | 1465.7 |  |  |  |  |
| Mean | 1518.2 | 1999.0 | 1027.2 |  |  |  |
| Combined Mean | 1516.6 | 2136.1 | 1091.6 | 1484.9 | 1676.2 | 2021.0 |

TABLE D

Glucose Oxidase Activity in U/ml versus time of storage at 25° C.

| Activity (U/ml) | 0 | 2 | 3 | 6 | 12 |
|---|---|---|---|---|---|
| Dil 1 | 1673.8 | 1698.8 | 2234.6 | 2265.7 | 1349 |
|  | 1554.3 | 1762.7 | 2007.9 | 2135.5 | 1675 |
|  | 1534.9 | 1689.0 | 2076.3 | 2133.1 | 1583 |
|  | 1268.6 |  |  |  |  |
| Mean | 1507.9 |  |  |  | 1535 |
| Dil 2 | 1705.3 | 1553.6 | 1685.9 | 2258.3 | 1147 |
|  | 1457.6 | 1805.6 | 1675.3 | 2201.4 | 1451 |
|  | 1492.3 | 1748.1 | 1673.6 | 2194.8 | 1635 |
| Mean | 1551.7 |  |  |  | 1411 |
| Combined Mean | 1529.8 | 1710.0 | 1892.2 | 2198.1 | 1473 |

TABLE E

Glucose Oxidase Activity in U/ml versus time of storage at 25° C.

| Activity (U/ml) | 0 | 2 | 3 | 6 |
|---|---|---|---|---|
| Dil 1 | 1673.8 | 1217.8 | 957.5 | 483.8 |
|  | 1554.3 | 1206.5 | 947.7 | 514.8 |
|  | 1534.9 | 1174.9 | 881.6 | 463.7 |
|  | 1268.6 |  |  |  |
| Mean | 1507.9 |  |  |  |
| Dil 2 | 1705.3 | 1142.8 | 1095.3 | 444.7 |
|  | 1457.6 | 1133.9 | 1073.8 | 440.5 |
|  | 1492.3 | 1159.6 | 991.7 | 427.8 |
| Mean | 1551.7 |  |  |  |
| Combined Mean | 1529.8 | 1173.0 | 991.3 | 462.5 |

What is claimed is:

1. A stabilized aqueous enzyme concentrate composition which comprises:

a) 1000 to 1800 units/ml of lactoperoxidase;

b) 1500 to 2750 units/ml of glucose oxidase;

c) 10 to 20% w/v of an alkali metal halide salt; and d) a chelating buffering agent present in an amount such that the pH of the composition is in the range of 5.5 to 6.5.

2. A composition as claimed in claim 1 which is stable for at least 6 months.

3. A composition as claimed in claim 1 wherein the activities of lactoperoxidase and glucose oxidase are maintained at at least 75% of their original activity after storage for 6 months at 25° C.

4. A composition as claimed in claim 1 wherein the alkali metal salt is sodium chloride.

5. A composition as claimed in claim 4 wherein concentration of sodium chloride is 14 to 16% w/v.

6. A composition as claimed in claim 1 in which the buffering agent is a sodium citrate.

7. A composition as claimed in claim 6 in which said sodium citrate is trisodium citrate which is present in an amount in the range 0.5 to 1.5% w/v.

8. A composition as claimed in claim 6 which also contains monosodium orthophosphate in an amount ranging from 0.05 M to 0.5 M.

* * * * *